(12) United States Patent
Catena Ruiz et al.

(10) Patent No.: US 8,492,402 B2
(45) Date of Patent: Jul. 23, 2013

(54) STABLE CRYSTALLINE SALT OF (R)-3-FLUOROPHENYL-3,4,5-TRIFLUOROBENZYLCARBAMIC ACID 1-AZABICYCLO [2.2.2]OCT-3-YL ESTER

(75) Inventors: Juan Lorenzo Catena Ruiz, Esplugues de Llobregat (ES); José Hidalgo Rodriguez, Esplugues de Lilobregat (ES); María del Carmen Serra Comas, Esplugues de Llobregat (ES); Isabel Masip Masip, Esplugues de Llobregat (ES)

(73) Assignee: Laboratorios Salvat, S.A., Esplugues de Llobregat (Barcelona)

( * ) Notice: Subject to any disclaimer, the term of this patent is extended or adjusted under 35 U.S.C. 154(b) by 236 days.

(21) Appl. No.: 12/744,493

(22) PCT Filed: Nov. 26, 2008

(86) PCT No.: PCT/EP2008/010012
§ 371 (c)(1),
(2), (4) Date: Aug. 10, 2010

(87) PCT Pub. No.: WO2009/068253
PCT Pub. Date: Jun. 4, 2009

(65) Prior Publication Data
US 2011/0207769 A1      Aug. 25, 2011

(30) Foreign Application Priority Data
Nov. 28, 2007   (EP) .................................... 07384038

(51) Int. Cl.
*A01N 43/90*    (2006.01)
*A61K 31/44*    (2006.01)
*C07D 453/02*   (2006.01)

(52) U.S. Cl.
USPC .......................................... 514/305; 546/137

(58) Field of Classification Search
USPC ........................................ 514/305; 546/137
See application file for complete search history.

(56) References Cited

U.S. PATENT DOCUMENTS 7,115,629 B2 * 10/2006  Farrerons Gallemi et al. ............................ 514/305
2004/0063950 A1  4/2004  Farrerons Gallemi et al.

FOREIGN PATENT DOCUMENTS

| EP | 1300407 A1 | 4/2003 |
| WO | 03/053966 A2 | 7/2003 |
| WO | 2004/000840 A2 | 12/2003 |

OTHER PUBLICATIONS

Andersson, Karl-Erik; "Overactive Bladder—New Antimuscarinics for Treatment," Business Briefing: North American Pharmacotherapy, 2004, Issue 2, pp. 1-6.
Hegde, Sharath, et al.; "Antimuscarinics for the treatment of overactive bladder: Current options and emerging therapies," Current Opinion in Investigational Drugs, 2004, pp. 40-49, vol. 5.
Andersson, Karl-Erik; "Anitmuscarinics for treatment of overactive bladder," The Lancet Neurology, 2004, pp. 46-53, vol. 3.
Press Release, "SVT-40776 successfully completes Phase I," states that SVT-40776 (i.e. tarafenacin) is a selective M3 muscarinic antagonist for the treatment of urinary incontinence. http://pharmalicensing.com/public/press/view/1087210751_40cd84ffbfdd7/svt-40776-successfully-completes-phase-i, (Jun. 14, 2004).
Clinical Trial, (outlined in ClinicalTrials.gov) was started on Jul. 2007 to determine the best dose of SVT-40776 in terms of efficacy, safety and tolerability in the treatment of overactive bladder is to be studied. http://clincaltrials.gov/ct2/show/NCT00507169.
Castellani, John J., "More Than 800 Medicines Are in Testing for Diseases Disproportionately Affecting American Women," Medicines in Development for Women, 2011, pp. 1-70.

* cited by examiner

*Primary Examiner* — Niloofar Rahmani
(74) *Attorney, Agent, or Firm* — Tristan A. Fuierer; Moore & Van Allen, PLLC

(57) ABSTRACT

The present invention refers to a stable crystalline salt of (R)-3-fluorophenyl-3,4,5-trifluorobenzylcarbamic acid 1-azabicyclo[2.2.2]oct-3-yl ester and its use as medicament, in particular for the treatment of urinary incontinence or other diseases involving genitourinary disorders.

6 Claims, 14 Drawing Sheets

STABLE CRYSTALLINE SALT OF (R)-3-FLUOROPHENYL-3,4,5-TRIFLUOROBENZYLCARBAMIC ACID 1-AZABICYCLO [2.2.2]OCT-3-YL ESTER

CROSS-REFERENCE TO RELATED APPLICATIONS

This application is filed under the provisions of 35 U.S.C. §371 and claims the priority of International Patent Application No. PCT/EP2008/010012 filed on 26 Nov. 2008 entitled "Stable Crystalline Salt of (R)-3-Fluorophenyl-3,4,5-Trifluorobenzylcarbamic Acid 1-Azabicyclo[2.2.2]Oct-3-yl Ester" in the name of Juan Lorenzo Catena Ruiz, et al., which claims priority of European Patent Application No. 07384038.1 filed on 28 Nov. 2007, both of which are hereby incorporated by reference herein in their entirety.

FIELD OF THE INVENTION

The present invention relates to a stable crystalline salt of (R)-3-fluorophenyl-3,4,5-trifluorobenzylcarbamic acid 1-azabicyclo[2.2.2]oct-3-yl ester and to pharmaceutical formulations of this salt, in particular for medical use including treatment of urinary incontinence urge or other diseases involving genitourinary disorders.

BACKGROUND OF THE INVENTION

WO00200652 discloses compound I ((R)-3-fluorophenyl-3,4,5-trifluorobenzylcarbamic acid 1-azabicyclo[2.2.2]oct-3-yl ester) which has the following formula (I)

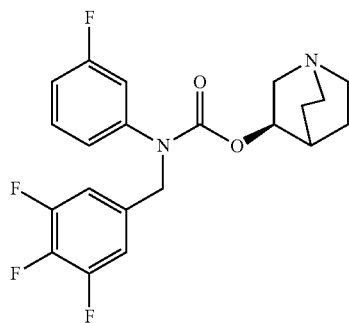

Compound I is also disclosed in WO2004000840. On the other hand, compound I is exemplified as hydrochloride salt in WO2003053966 as an intermediate in the synthesis of other compounds. However, this acid addition salt known from the prior art had the disadvantage that its physicochemical stability was poor. Upon storage or formulation of said known salt, progressive decomposition and concomitantly an increase in the amount and number of impurities was observed. Obviously, this problem is further aggravated under demanding environmental conditions such as light, heat, humidity or acidity.

SUMMARY OF THE INVENTION

It has been particularly difficult to find stable, crystalline forms of (R)-3-fluorophenyl-3,4,5-trifluorobenzylcarbamic acid 1-azabicyclo[2.2.2]oct-3-yl ester. The hydrochloride salt of compound I has the disadvantage of being highly hygroscopic, and when purified, the initial white foam quickly becomes a sticky gum due to its humidity uptake. Thus, there remains a need for a salt of (R)-3-fluorophenyl-3,4,5-trifluorobenzylcarbamic acid 1-azabicyclo[2.2.2]oct-3-yl ester that forms a crystalline solid that has a desirable morphology, be stable in the presence of water and under conditions of a high relative humidity (above 85%) and can readily be prepared on a large scale.

It has now been found that the above mentioned problem can be solved with the D-tartrate salt of compound I. The D-tartrate salt is more stable than the hydrochloride salt at room, enhanced temperature and at relative high humidity and in aqueous media. In addition, this D-tartrate salt in crystalline form has also been found to be stable, highly soluble in water and easy to handle or process.

Thus, a first aspect of the invention relates to a D-tartrate salt of compound I, ((R)-3-fluorophenyl-3,4,5-trifluorobenzylcarbamic acid 1-azabicyclo[2.2.2]oct-3-yl ester) of structural formula (II):

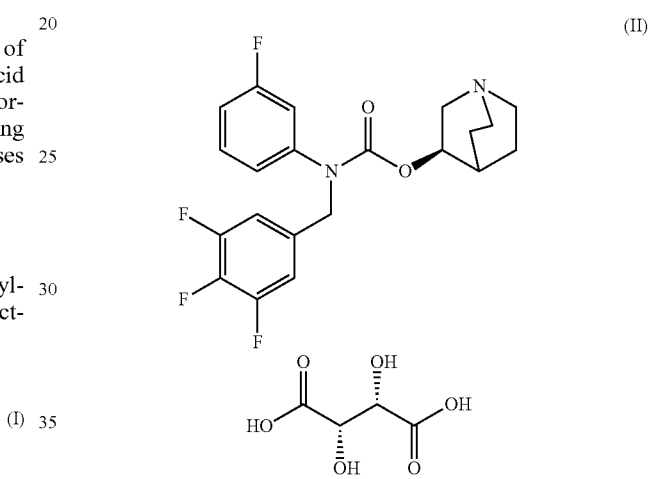

possessing a stoichiometry of substantially 1:1 of compound I to D-tartaric acid, and in the form of crystalline polymorph I, which is characterized by an X-Ray powder diffractogram pattern with peaks at °2θ as shown in FIG. 1.

A second aspect of the invention relates to a pharmaceutical composition comprising a D-tartrate salt of compound I as described above, with at least one pharmaceutically acceptable carrier or excipient.

A third aspect of the invention relates to a D-tartrate salt of compound I as described above for use as a medicament.

A further aspect of the invention relates to the use of a D-tartrate salt of compound I as described above in the preparation of a medicament for the treatment of a disease or condition involving genitourinary disorders, in particular for the treatment of urinary incontinence, and more particularly for the treatment of overactive bladder.

A further aspect of the invention relates to a method for the treatment of a disease or condition involving genitourinary disorders, in particular for the treatment of urinary incontinence, and more particularly for the treatment of overactive bladder, comprising administering to a subject in need thereof a therapeutically effective amount of a D-tartrate salt of compound I as described above.

Figure 1:
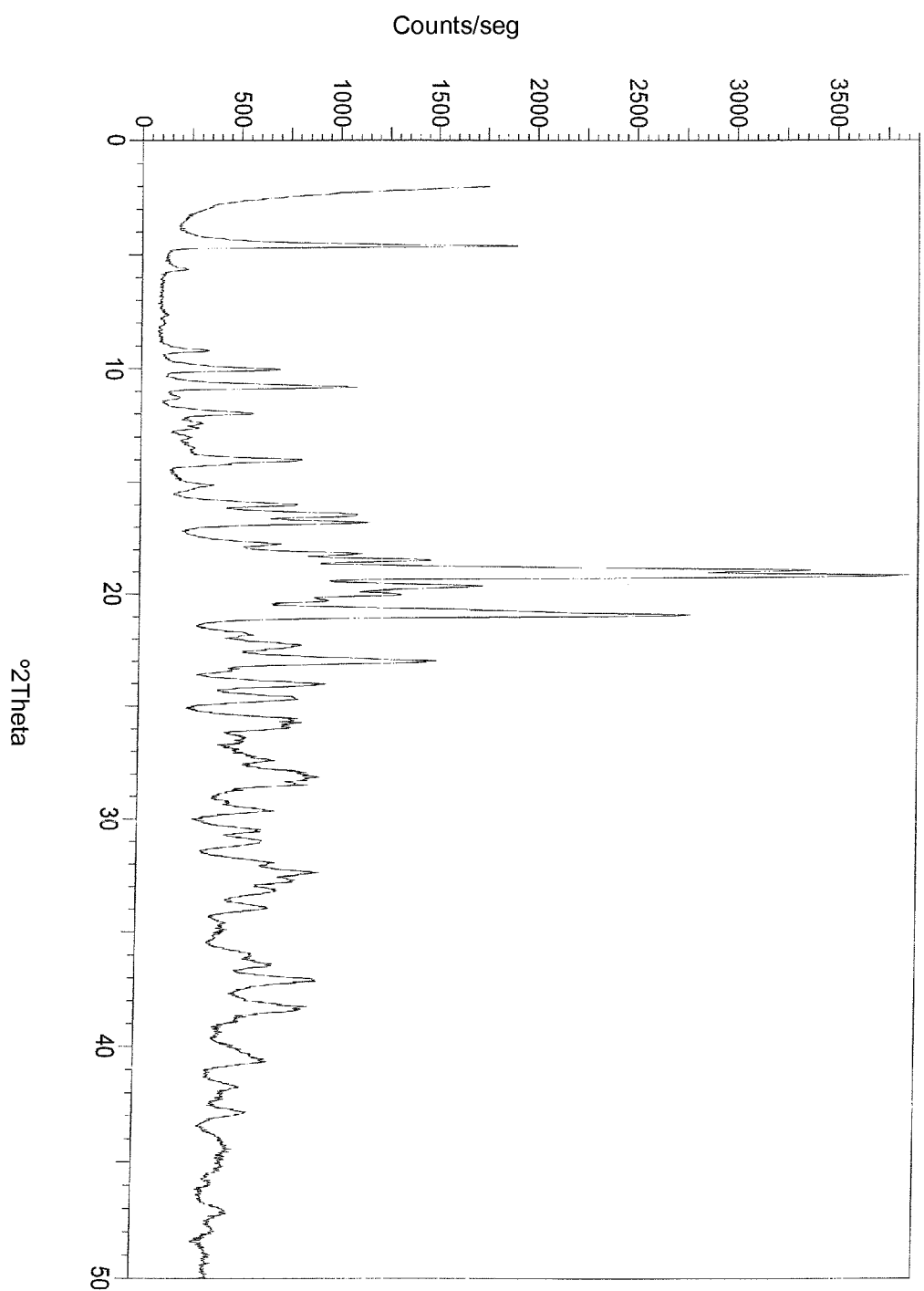
FIG. 1: Shows an X-ray powder diffractogram (XRPD) of a crystalline D-tartrate salt of compound I, polymorph I (obtained using copper Kα radiation) prepared in Example 2.
Figure 2:
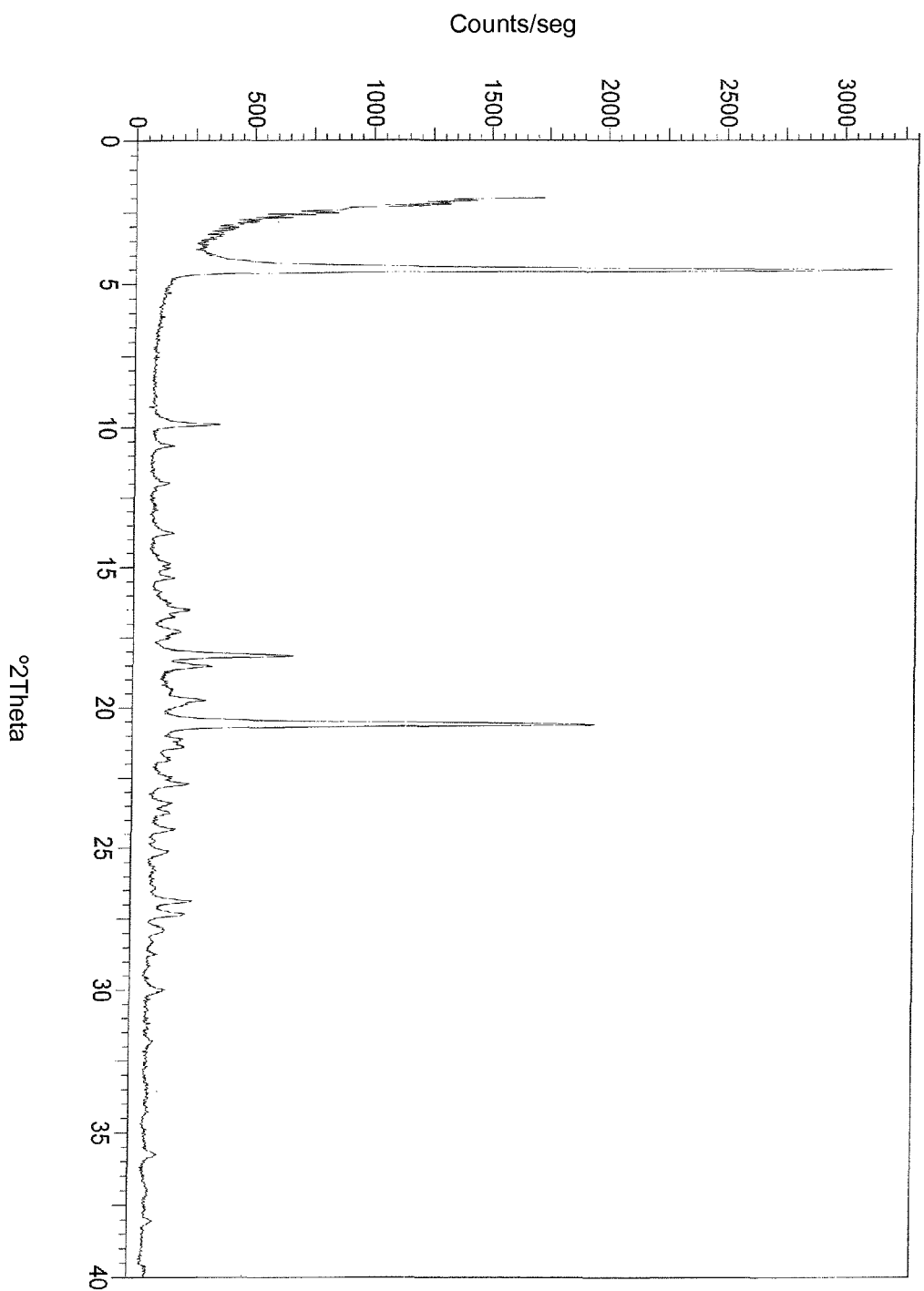
FIG. 2: Shows an X-ray powder diffractogram (XRPD) of a crystalline D-tartrate salt of compound I, polymorph II (obtained using copper Kα radiation) prepared in Example 3.

Further details for the figures are revealed in the Examples below.

DETAILED DESCRIPTION OF THE INVENTION

The present invention relates to a D-tartrate salt of compound I. D-tartrate provides optimal properties for formulation due to its stability, and it has the structural formula (II):

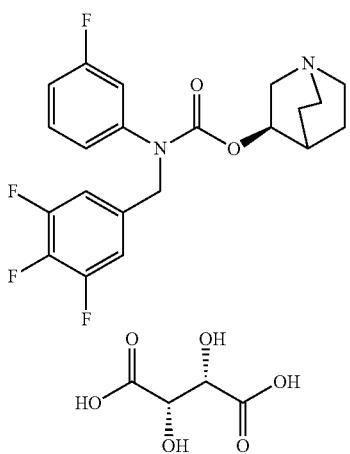

(II)

In order to be considered as a candidate for further development as a pharmaceutical, a compound must not only possess desirable biological properties, but also physical properties that permit its use in the manufacture of a pharmaceutical composition. In particular, the compound should form a stable, preferably crystalline, solid that can be readily manufactured and formulated.

Salt formation studies provide a means of altering the physicochemical and resultant biological characteristics of a drug without modifying its chemical structure. A salt form can have a dramatic influence on the properties of the drug. The selection of a suitable salt is partially dictated by yield, rate and quantity of the crystalline structure. In addition, hygroscopicity, stability, solubility and the process profile of the salt form are important considerations. Solubility of a salt form can affect its suitability for use as a drug. Where aqueous solubility is low, i.e. less than 10 mg/ml, the dissolution rate at in vivo administration can be rate limiting in the absorption process leading to poor bioavailability. Hygroscopicity is also an important characteristic. Compounds having low hygroscopicity tend to have better stability and easier processing. Stability at low and high relative humidity is desirable in a product to be used or sold in a wide diversity of environments.

The inventors have found that it is difficult to obtain a suitable salt of compound I for pharmaceutical formulation. The present invention has overcome these problems with the D-tartrate salt disclosed herein, which is crystalline, is relatively non-hygroscopic, and generally has better physical properties than other salts of the compound. Also, it has been found that the final content of impurities may be significantly reduced by precipitation of the D-tartrate salt of compound I as described herein.

To select the most suitable salt of compound I and minimize the undesirable hygroscopic properties of the hydrochloride, several acids were tested. The free base of compound I was dissolved in hot ethanol, and then acid solution in hot ethanol was added. The mixture was then stirred and heated for 30 min. After cooling to room temperature, the solvent was removed by evaporation. Acids tested included acetic, L-ascorbic, benzenesulphonic, (RS)-10-camphorsulfonic, (S)-10-camphorsulfonic, citric, embonic, fumaric, DL-lactic, L-lactic, maleic, D-malic L-malic, DL-malic, malonic, mandelic, D-mandelic, L-mandelic, methanesulphonic, orotic, oxalic, propionic, sorbic, succinic, DL-tartaric, L-tartaric and D-tartaric. The results concerning the salts obtained were as indicated in Table 1.

TABLE 1

| Acid | Aspect of the salt |
| --- | --- |
| Acetic | Hygroscopic white foam |
| L(+)-Ascorbic | White foam |
| Benzenesulphonic | Oil |
| (RS)-10-Camphorsulfonic | Hygroscopic pink foam |
| (S)-10-Camphorsulfonic | Oil |
| Citric | Oil |
| Embonic | Yellow solid |
| Fumaric (0.5 eq) | White foam |
| Fumaric | White foam |
| Hydrochloric | Hygroscopic white foam |
| DL-Lactic | Oil |
| L-Lactic | Oil |
| Maleic | Oil |
| D-Malic (0.5 eq) | Hygroscopic red foam |
| DL-Malic (0.5 eq) | Hygroscopic red foam |
| D-Malic | Hygroscopic red foam |
| L-Malic (0.5 eq) | Oil |
| L-Malic | Oil |
| DL-Malic | Hygroscopic red foam |
| Malonic | Oil |
| Mandelic | White foam |
| (S)-Mandelic | Oil |
| (R)-Mandelic | Oil |
| Methanesulphonic | Oil |

TABLE 1-continued

| Acid | Aspect of the salt |
|---|---|
| Orotic | Acid too insoluble in ethanol |
| Oxalic | Hygroscopic white foam |
| Propionic | Hygroscopic white foam |
| Sorbic | Oil |
| Succinic | Hygroscopic white foam |
| DL-Tartaric | Adding MTBE precipitated a white solid |
| L-Tartaric (0.5 eq) | White foam |
| D-Tartaric (0.5 eq) | White solid crystal precipitated in EtOH. |
| L-Tartaric | White foam |
| D-Tartaric | White solid crystal precipitated in EtOH. |

As indicated in Table 1, most of the acids tested yielded oils or hygroscopic foams, whereas salt obtained with D-tartaric acid was the only one to yield a non-hygroscopic solid crystal under these conditions.

D-tartaric acid is a dicarboxylic acid and thus it may form both hydrogentartarate and tartrate salts. The invention refers to both a salt in which the molar ratio of compound I to tartaric acid is about 1:1 (i.e., a hydrogentartarate) and a salt in which the molar ratio of compound I to tartaric acid is about 2:1 (i.e., a tartrate), as well as mixed salts, with for example an alkali metal or ammonium cation. The crystalline polymorphs (i.e. Forms I, II, III, and IV) of D-tartrate of compound I discussed below are hydrogentartarate salts, i.e., the molar ratio of compound I to tartaric acid is about 1:1.

Salts of the present invention can be crystalline and may exist as more than one polymorph. Hydrates as well as anhydrous forms of the salt are also encompassed by the invention. In particular the anhydrous form of the D-tartrate salt of compound I is preferred. In an embodiment of the invention, the salt is a substantially anhydrous crystalline salt.

D-tartaric acid salts may be formed by contacting stoichiometric amounts of the acid with compound I free base. Alternatively, the acid may be used in excess, usually no more than 1.25 equivalents. Preferably the base and/or the acid are in solution, more preferably both are in solution.

Broadly speaking, the crystalline salts of the invention may be prepared by mixing a solution of either reactant in solvent, i.e. a suitable single solvent or a suitable mixture of solvents, preferably at room temperature or at elevated temperature, or by adding a solution of either reactant to a solid form of the other reactant and with subsequent precipitation of the crystalline compound I salt. The term "a solvent" as used herein include both a single solvent or a mixture of different solvents. It is understood that the solvent may comprise water as the case may be, e.g. about 0-20% water. The term suitable solvent as used herein in relation to the preparation of the D-tartrate salt and the recrystallization defines any lower alkanol, water or ketone solvent in which the compound I is soluble and includes primary, secondary and tertiary alcohols and the corresponding ketones of from 1 to 6 carbon atoms. Suitable lower alkanol solvents include, but are not limited to, methanol, ethanol, 1-propanol, 2-propanol, 1-butanol, 2-butanol, 2-methyl-1-propanol, 1,1-dimethyl-ethanol and cyclohexanol.

Improved yield may be obtained by evaporation of some or all of the solvent or by crystallization at elevated temperatures followed by controlled cooling, preferably in stages. Careful control of precipitation temperature and seeding may be used to improve the reproducibility of the production process and the particle size distribution and form of the product. Particularly good yields have been obtained using EtOH as solvent.

Conveniently (R)-3-Fluorophenyl-3,4,5-trifluorobenzylcarbamic acid 1-azabicyclo[2.2.2]oct-3-yl ester and one equivalent of D-tartaric acid are dissolved in hot EtOH. Seeding with a small quantity of previously prepared crystals may help initiate crystallization.

The present invention also provides four crystalline polymorphic forms of D-tartrate of compound I (hereinafter referred to as Forms I, II, III, and IV, respectively).

The pharmaceutical composition of the present invention may comprise about 20, 30, 40, 50, 60, 70, 80, 90, 95, 96, 97, 98, 99, 99.1, 99.2, 99.3, 99.4, 99.5, 99.6, 99.7, 99.8, 99.9 or 100% by weight of Form I, II, III, or IV of D-tartrate of compound I, based upon 100% total weight of D-tartrate of compound I in the pharmaceutical composition (or the total weight of crystalline D-tartrate of compound I in the pharmaceutical composition).

Figure 3:
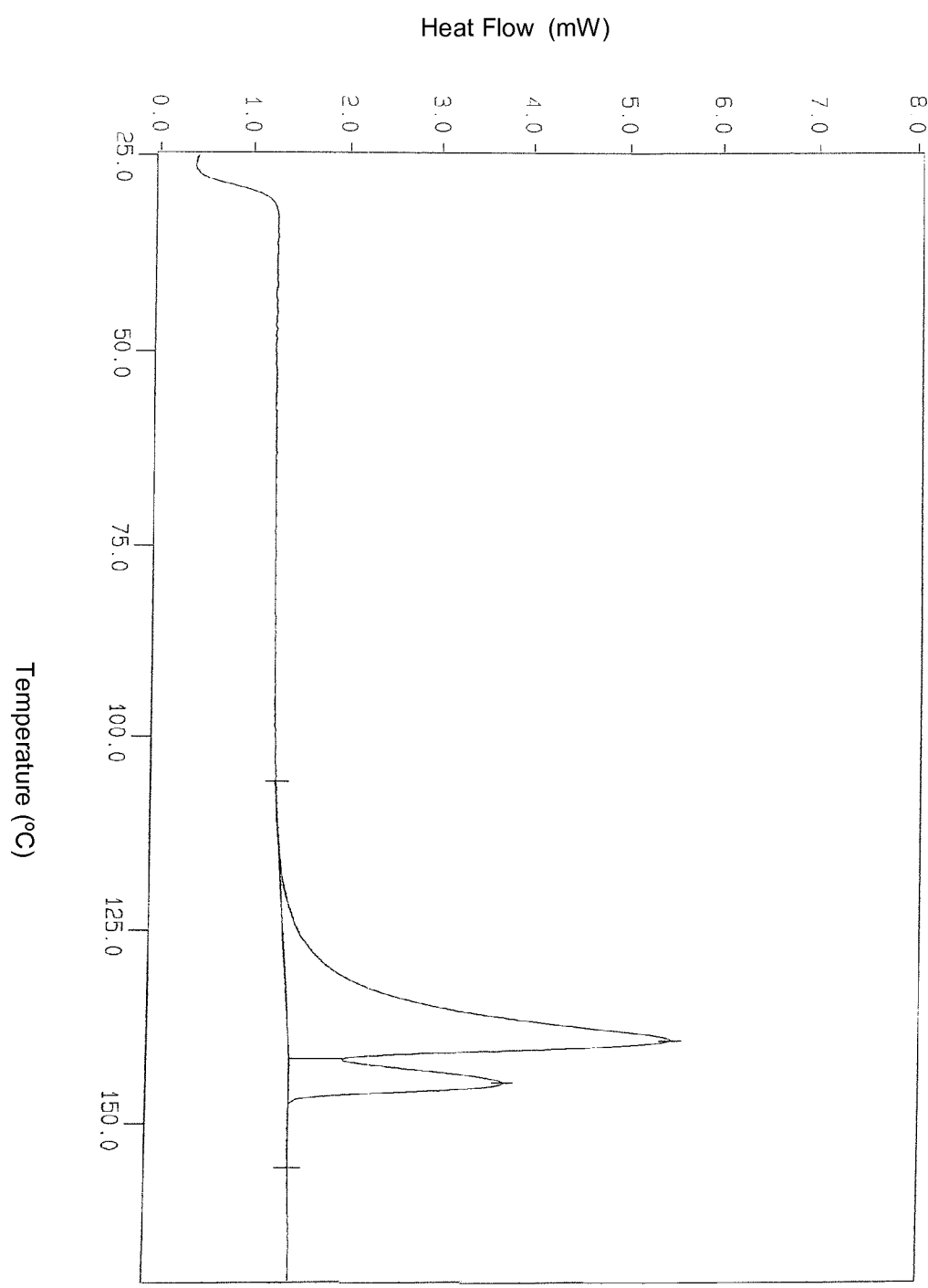
FIG. 3: Shows a DSC of a crystalline D-tartrate salt of compound I, prepared in Example 2.

Crystalline polymorph Form I of D-tartrate of compound I is stable at room temperature. Form I is physically stable at room temperature but it is enantiotropically related with Form II, this means that at room temperature Form I (lower melting polymorph) is the more stable one and at higher temperatures the higher melting polymorph (Form II) is the more stable one. According to Differential Scanning calorimetry (DSC), Form I has a double endotherm at about 139° C. and at about 145° C. (see FIG. 3).

Form I may be prepared from the free base of compound I as follows. The free base of compound I and D-tartaric acid are dissolved in hot ethanol. The solution is then slowly cooled (e.g., for 3 hours or longer) to yield Form I of D-tartrate of compound I. The crystals of Form I may be recovered by any method known in the art.

Form I can also be prepared by preparing a slurry containing Form II, Form III or Form IV, or a mixture thereof, with EtOH at room temperature.

Any crystal prepared by the aforementioned methods may be recovered by techniques known to those skilled in the art, such as, for example, filtration.

Figure 4:
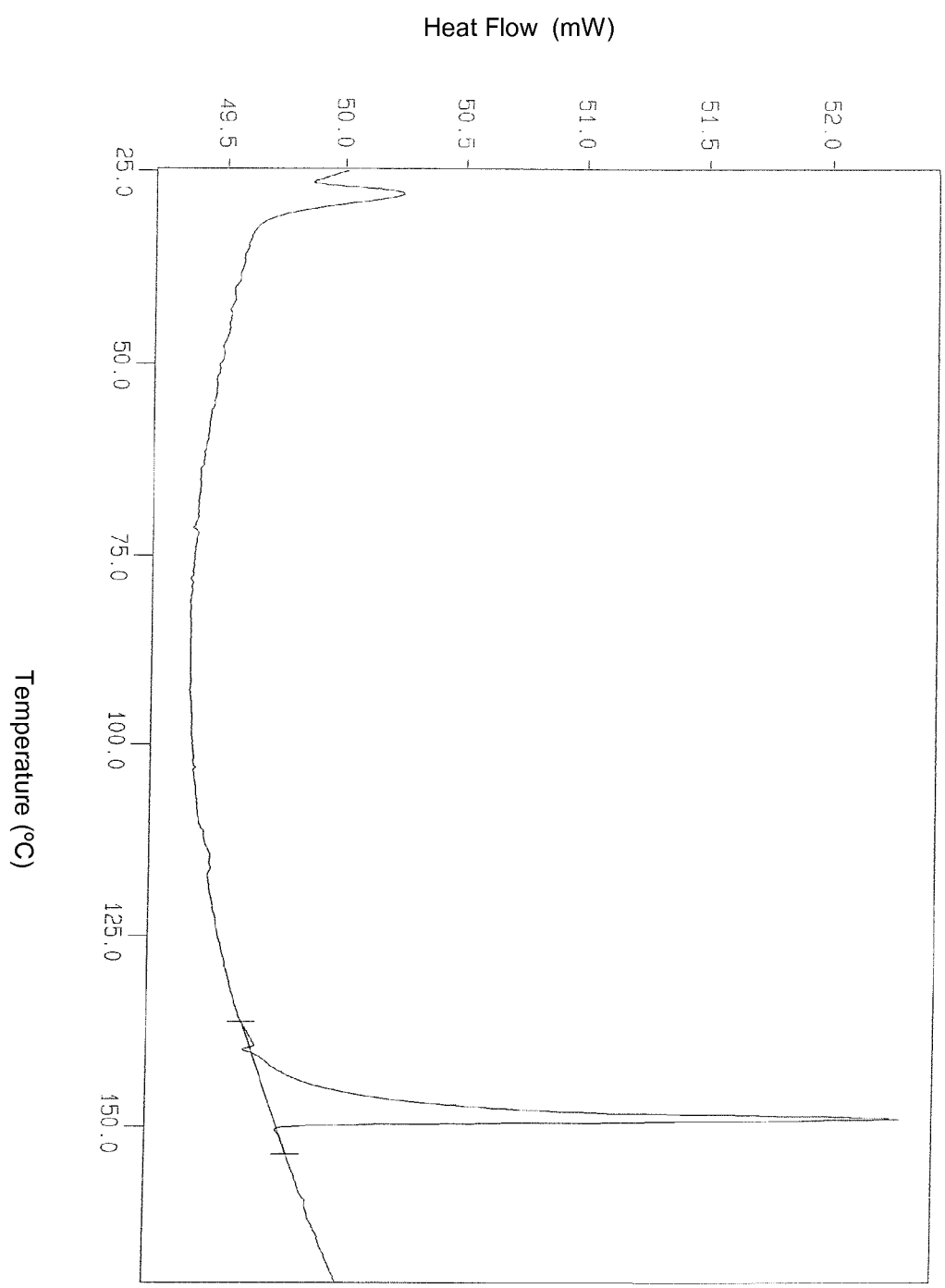
FIG. 4: Shows a DSC of a crystalline D-tartrate salt of compound I, prepared in Example 3.

Crystalline polymorph Form II of D-tartrate of compound I was obtained under controlled temperature conditions and according to DSC has an endotherm at about 149° C. (see FIG. 4).

Figure 5:
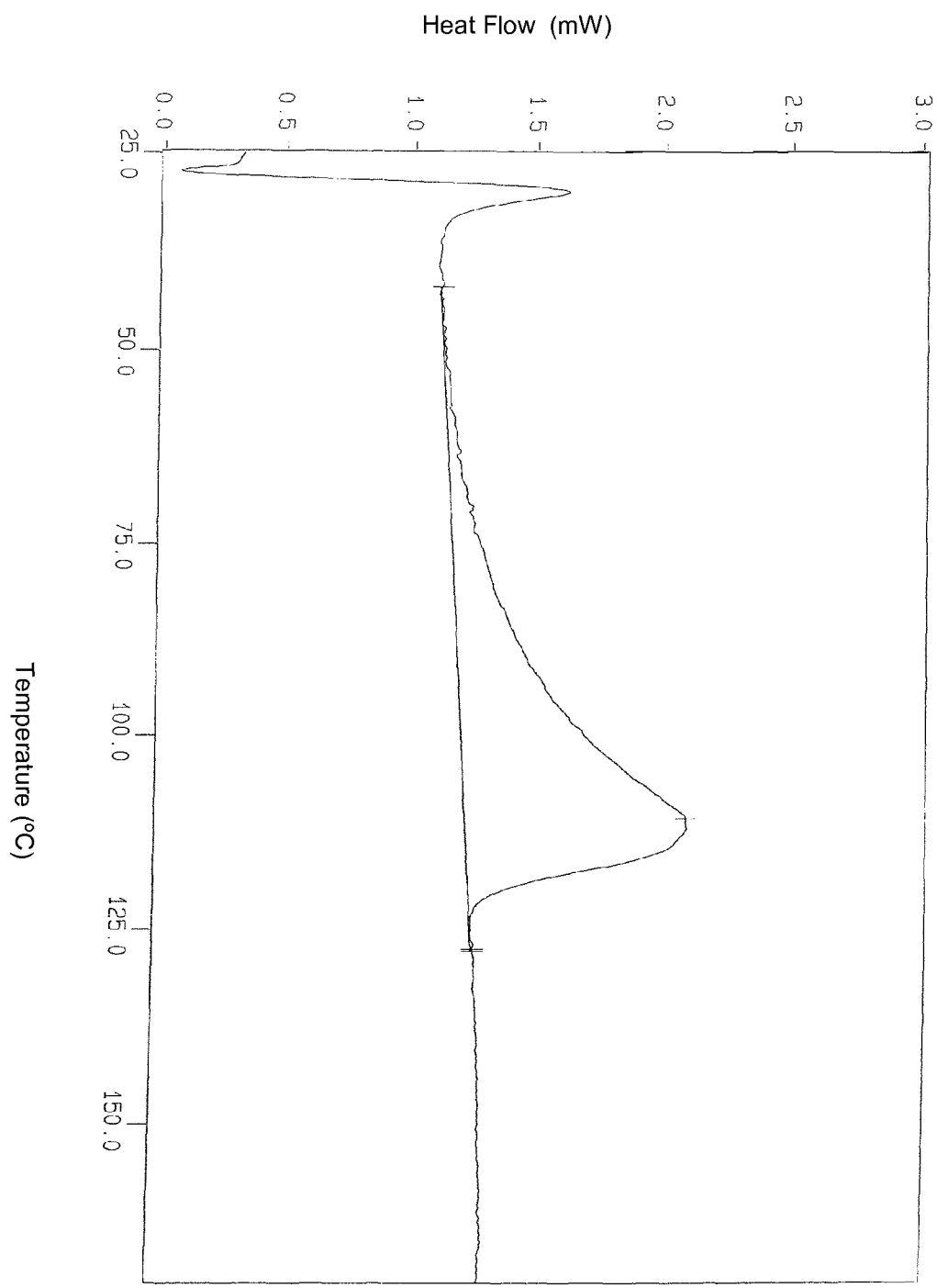
FIG. 5: Shows a DSC of a crystalline D-tartrate salt of compound I, prepared in Example 4.

Crystalline polymorph Form III of D-tartrate of compound I was obtained by equilibration in Water and according to DSC has an broad endotherm at about 110° C. (see FIG. 5).

Figure 6:
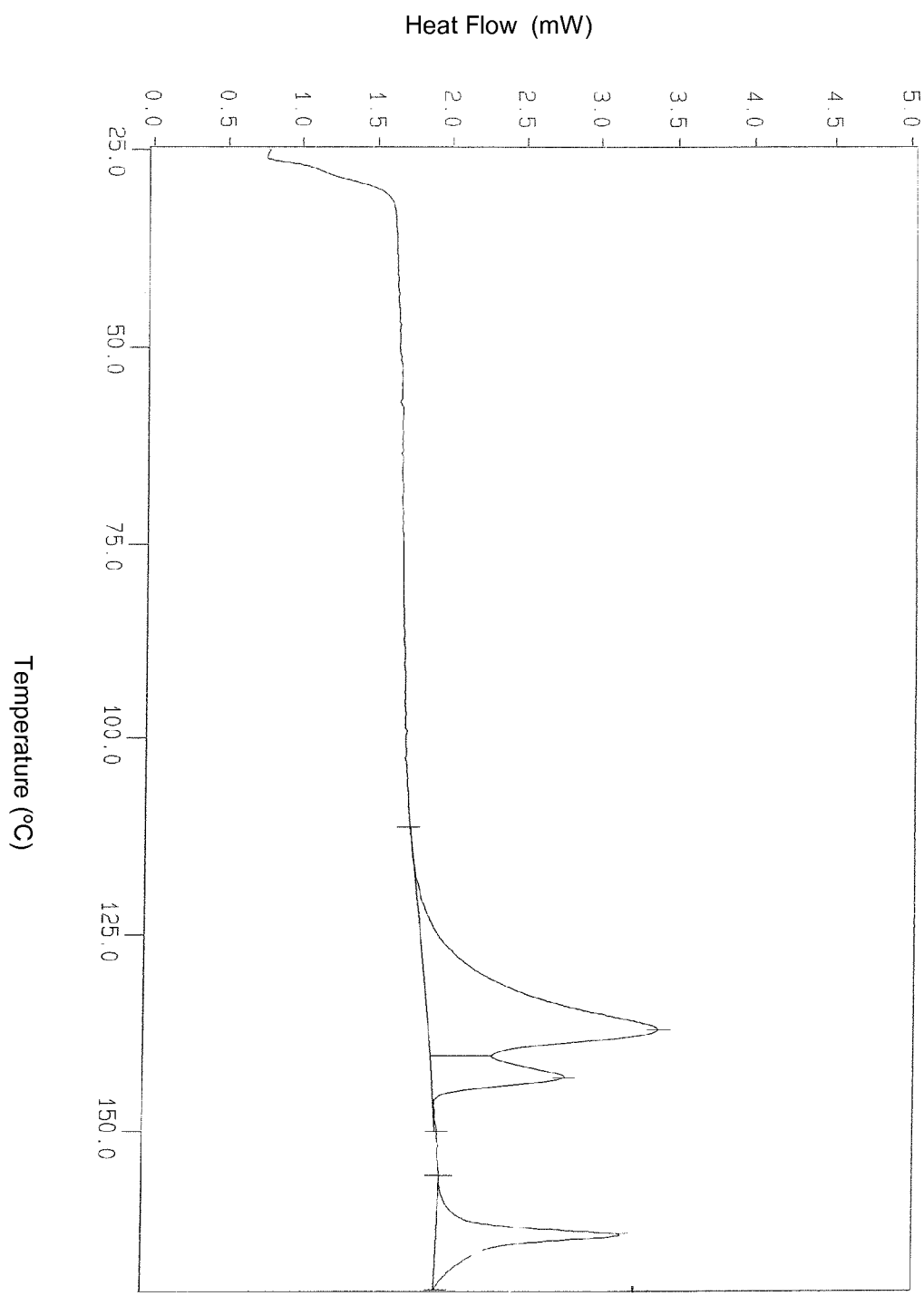
FIG. 6: Shows a DSC of a crystalline D-tartrate salt of compound I, prepared in Example 5.
Figure 7A:
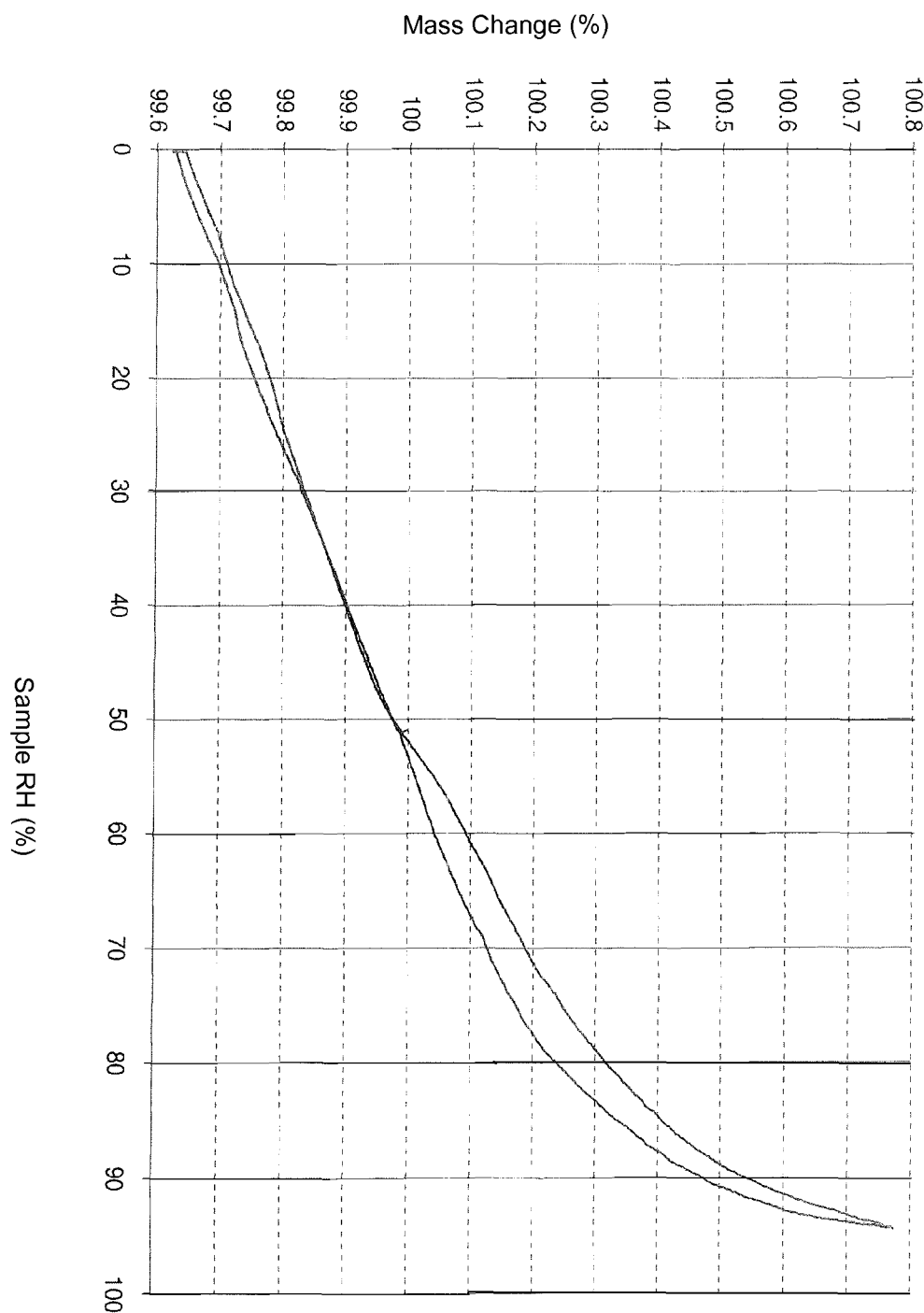
FIG. 7A shows the isotherms derived from the data shown in FIG. 7B by representing the equilibrium mass change values at each relative humidity step. Isotherms are divided into two components: sorption for increasing humidity steps and desorption for decreasing humidity steps.
Figure 7B:
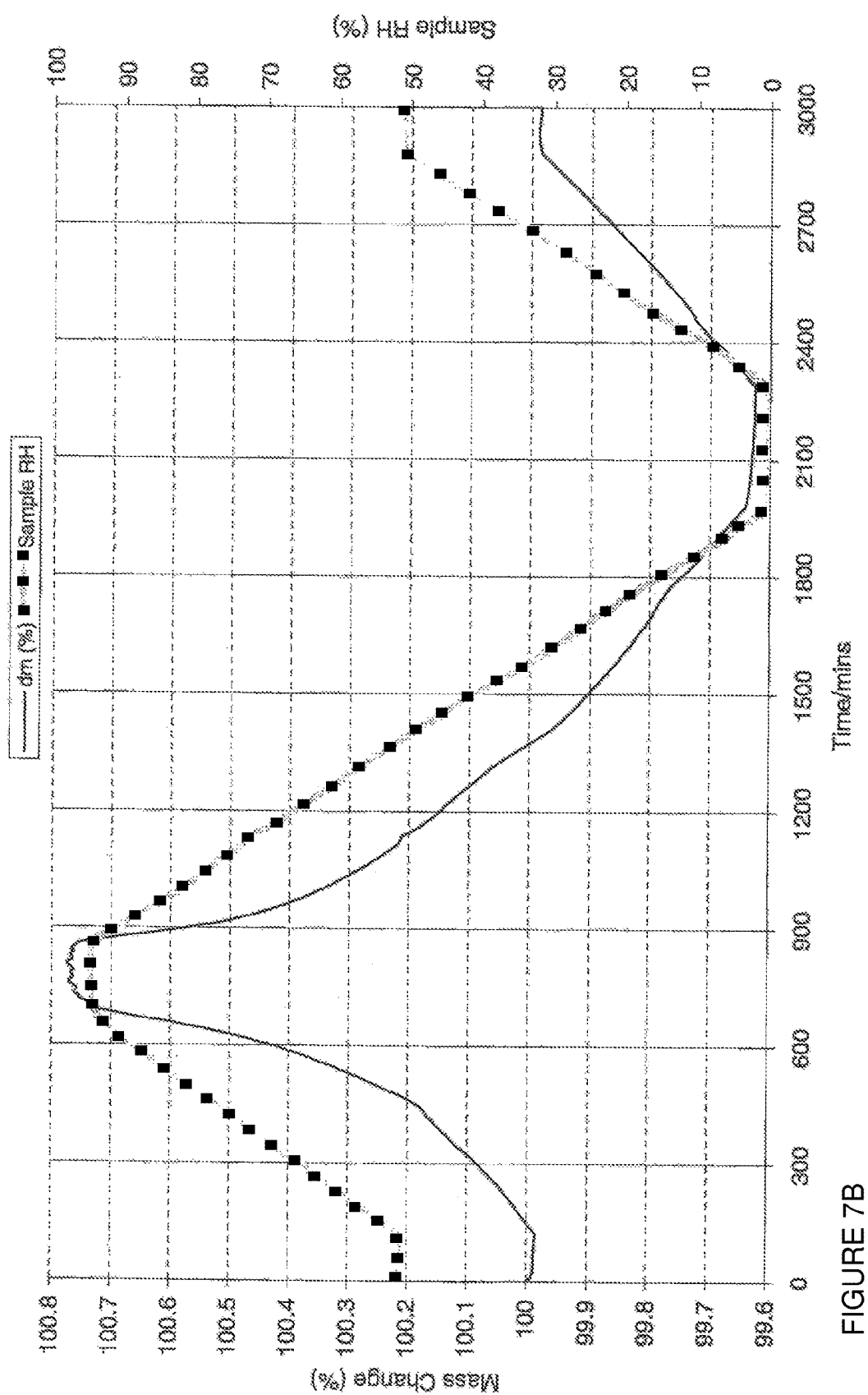
FIG. 7B shows the vapor sorption kinetic obtained by exposing the product to a series of step changes in relative humidity and monitoring the mass change as a function of time. The darker line represents the mass change of the product as a function of time and the lighter line with squares represents the relative humidity as a function of time.
Figure 8:
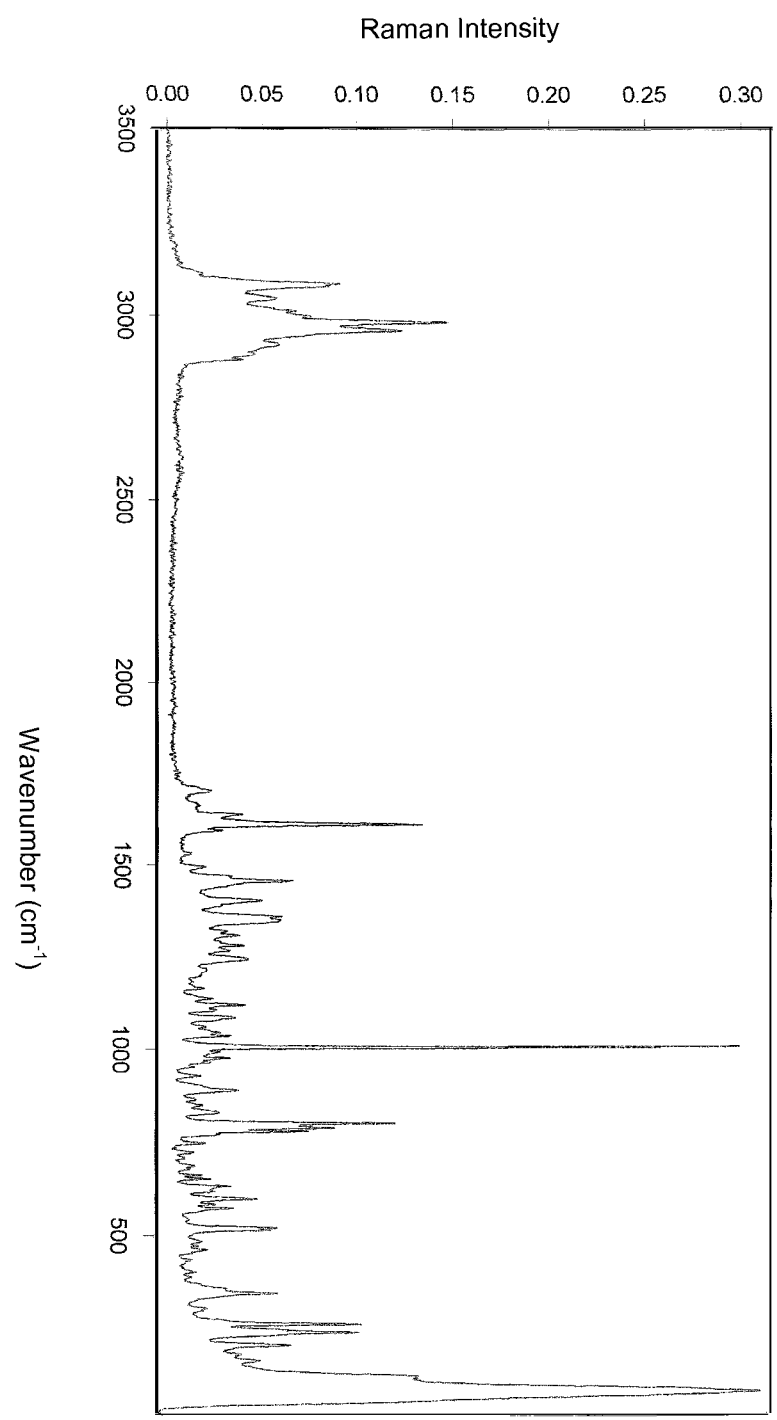
FIG. 8: Shows a FT-Raman of a crystalline D-tartrate salt of compound I, prepared in Example 1.
Figure 9:
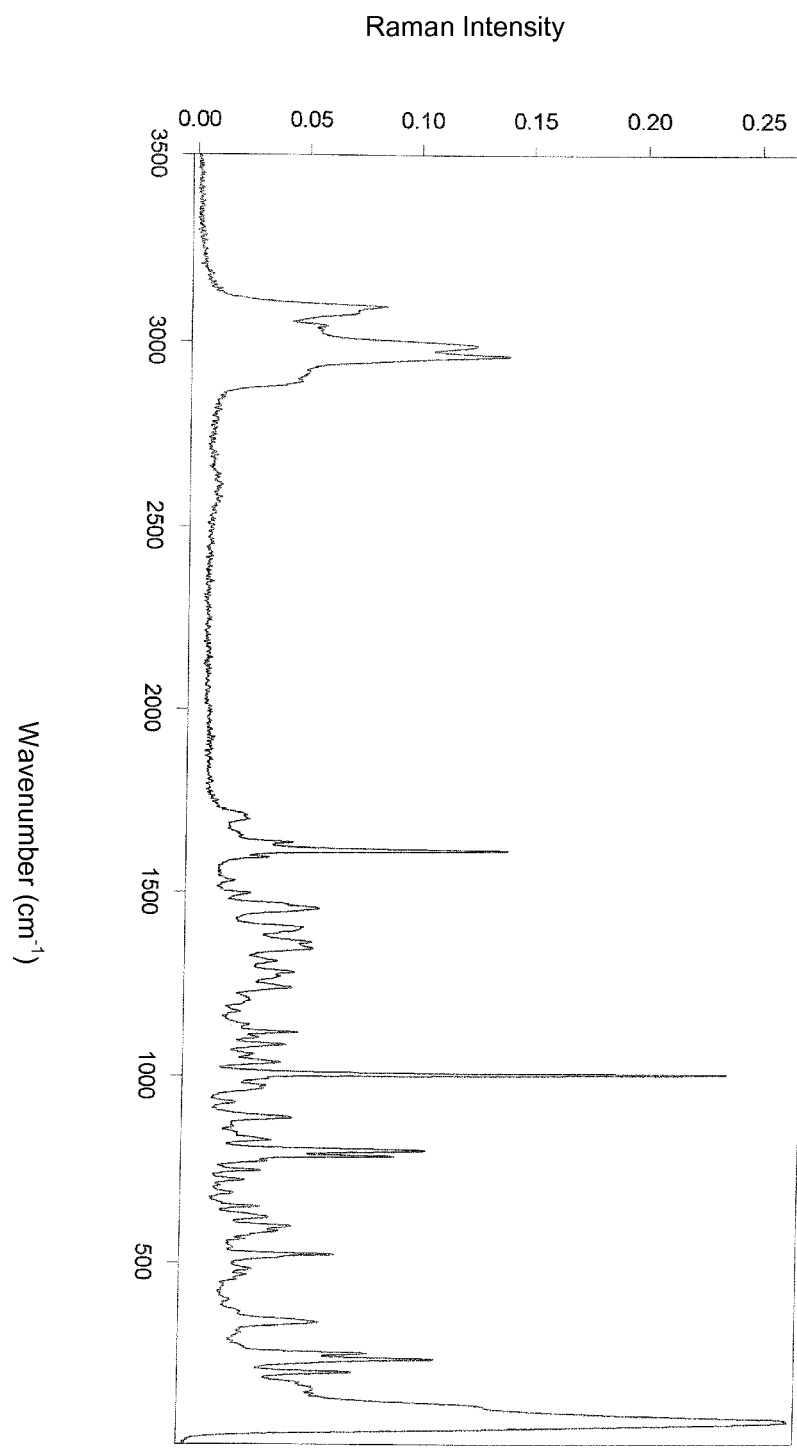
FIG. 9: Shows a FT-Raman of a crystalline D-tartrate salt of compound I, prepared in Example 3.
Figure 10:
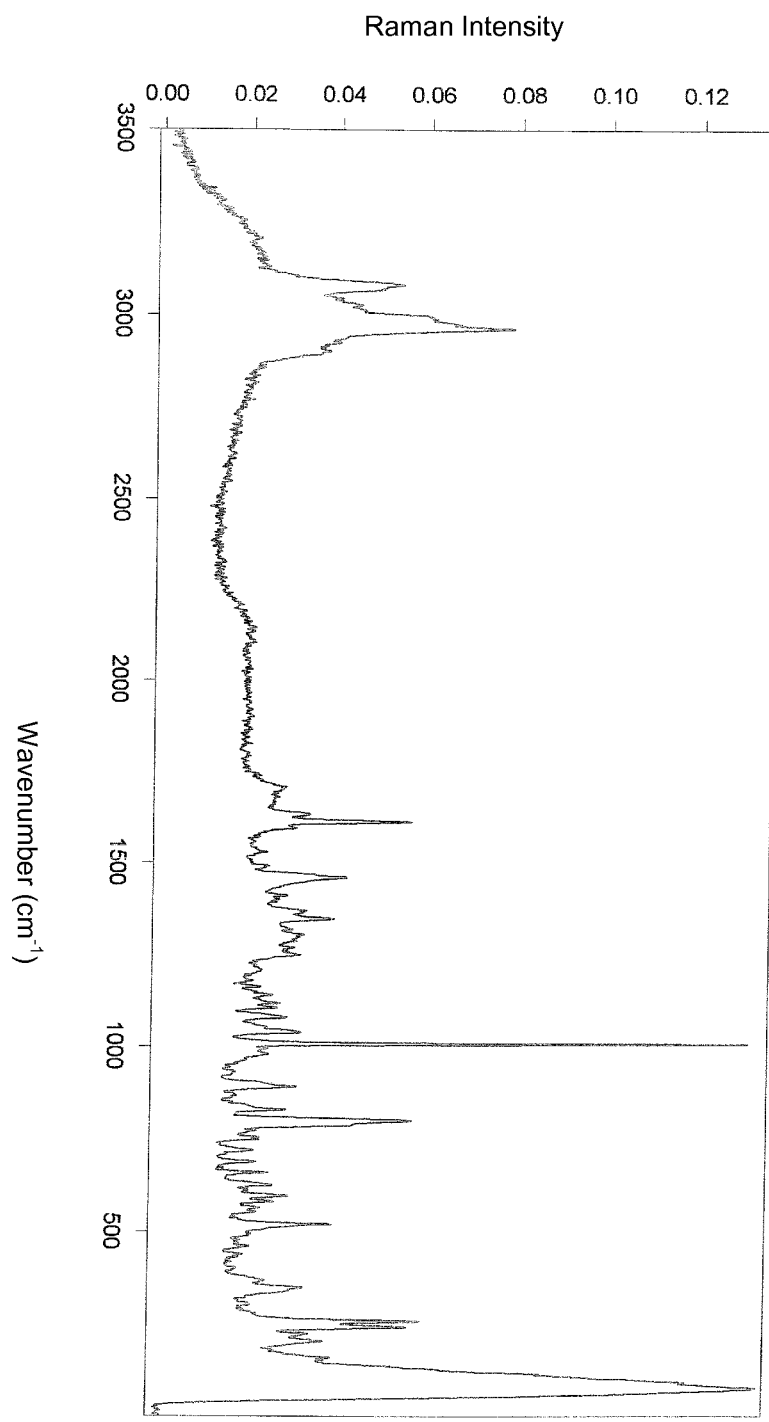
FIG. 10: Shows a FT-Raman of a crystalline D-tartrate salt of compound I, prepared in Example 4.
Figure 11A:
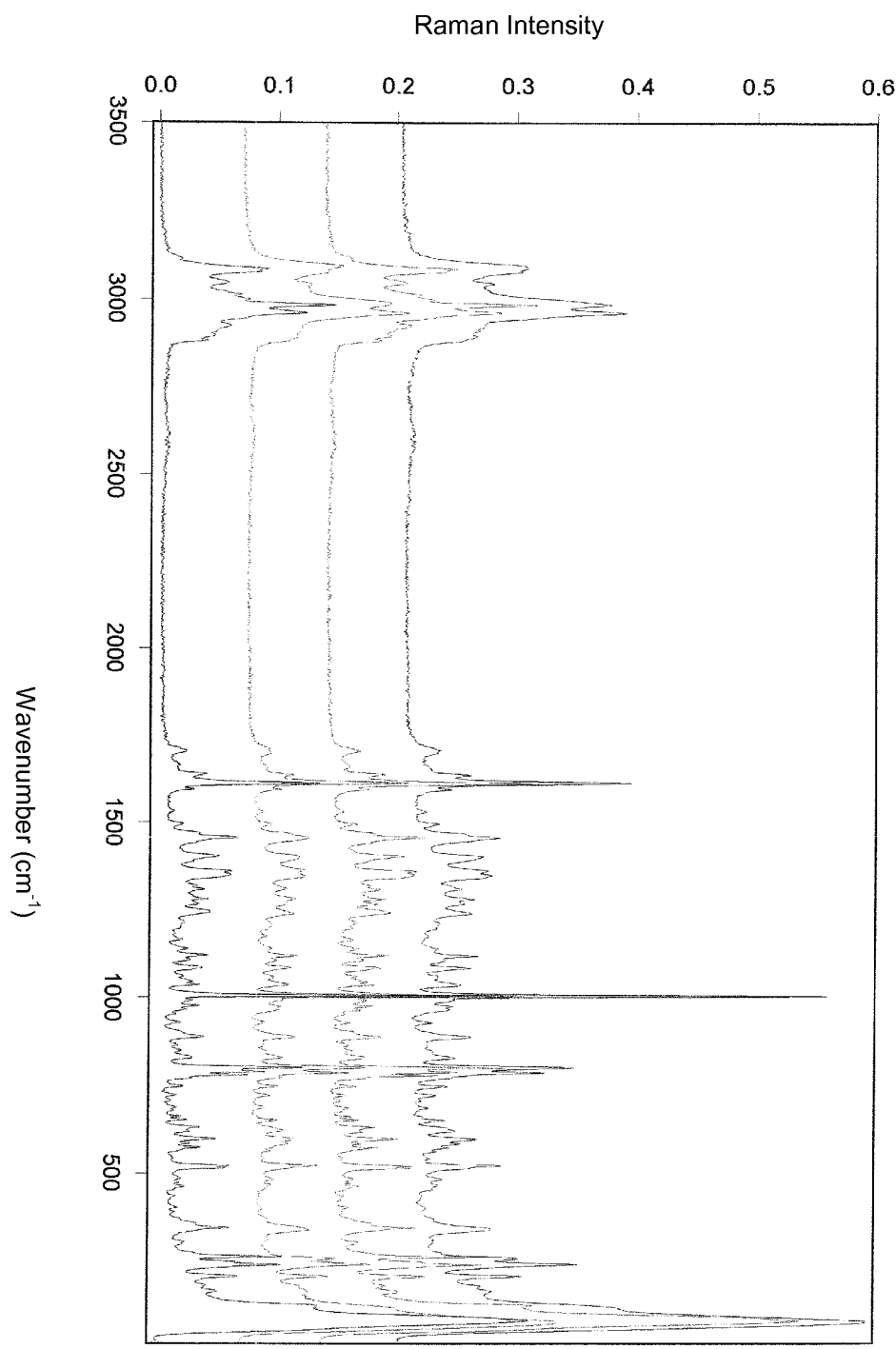
FIG. 11A: Shows FT-Raman differences between the different polymorphs (FIGS. 8, 9 and 10) for 1-3500 cm$^{-1}$.
Figure 11B:
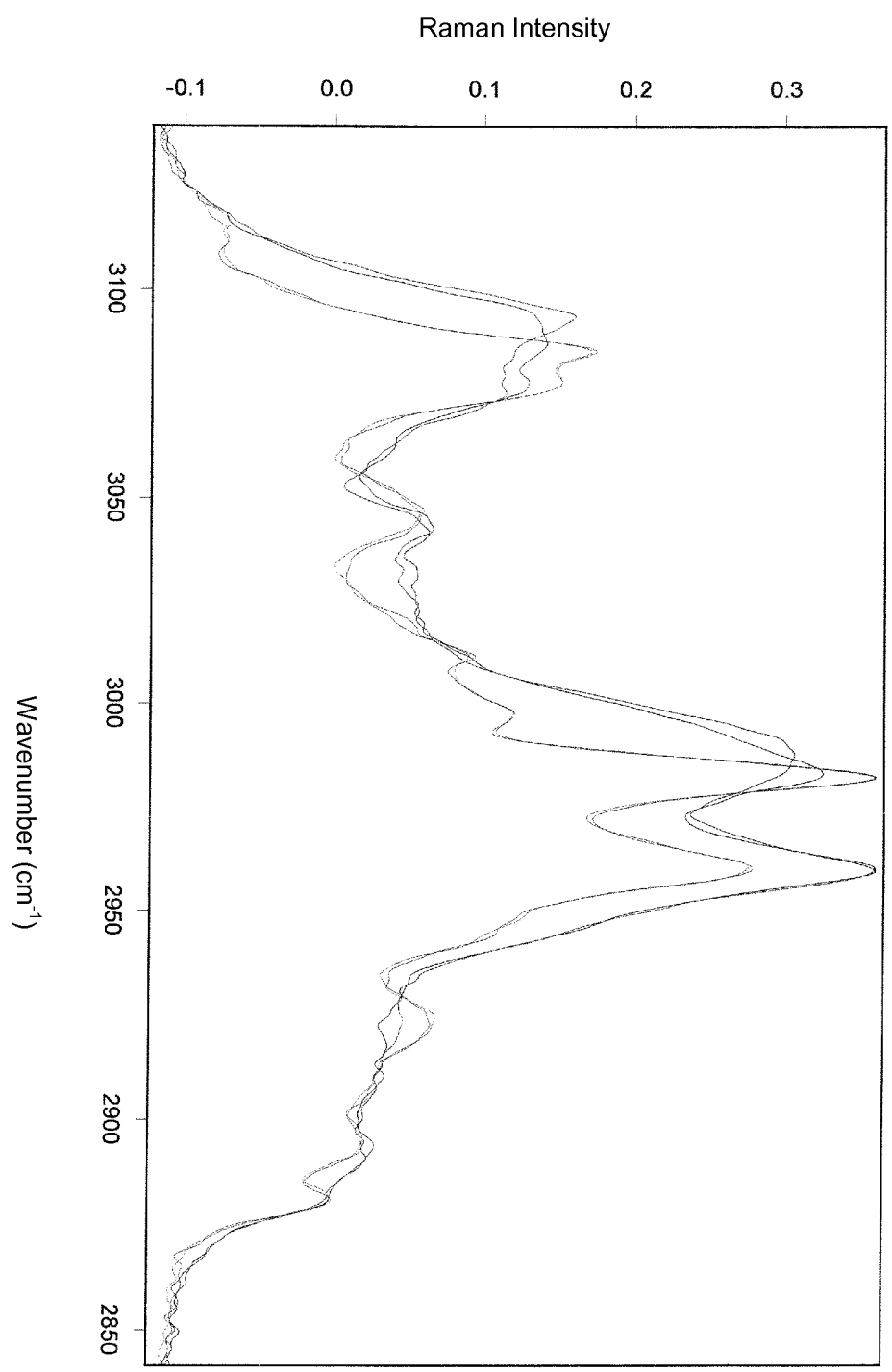
FIG. 11B: Shows FT-Raman differences between the different polymorphs (FIGS. 8, 9 and 10) for 2850-3150 cm$^{-1}$.
Figure 11C:
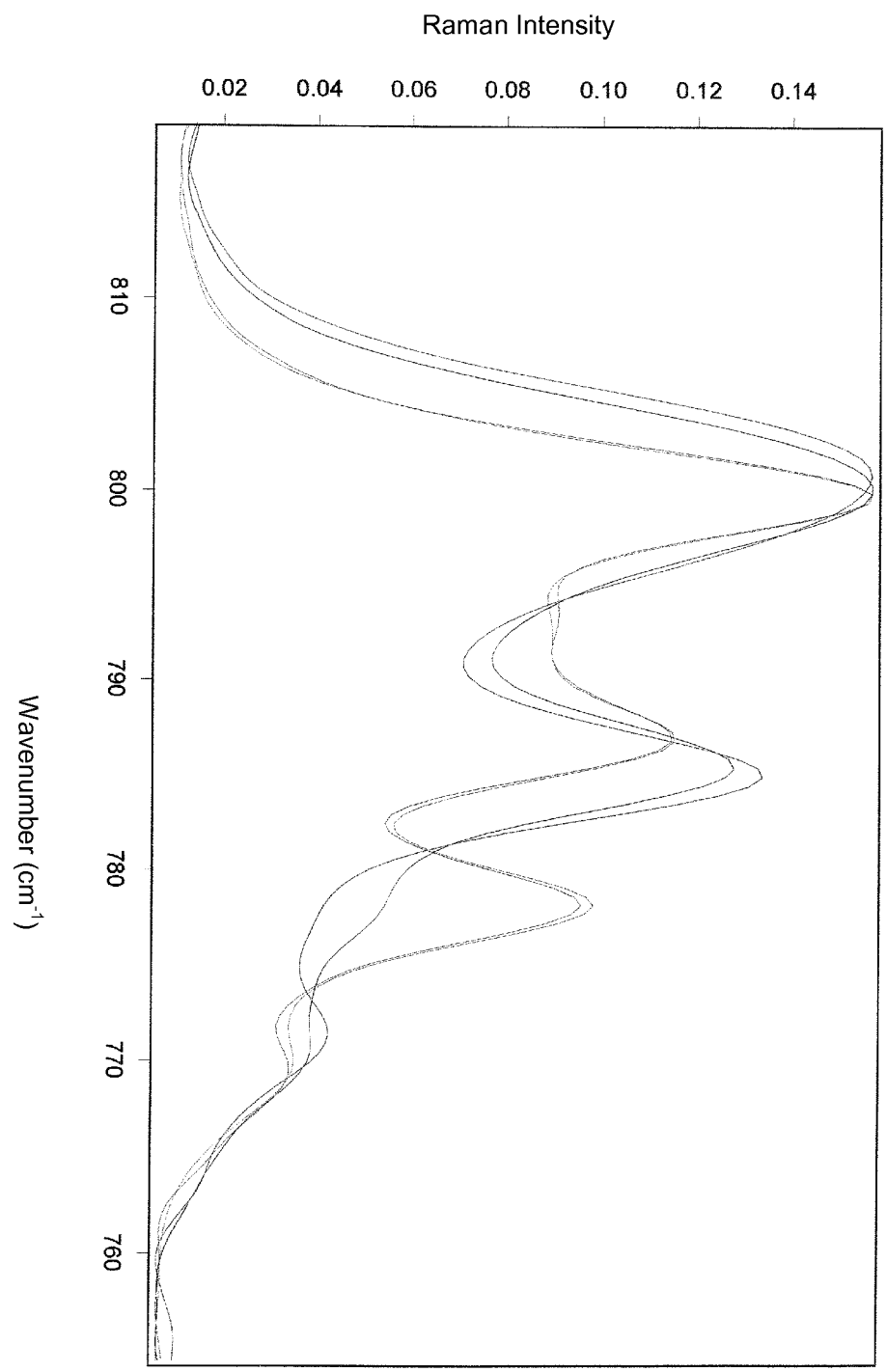
FIG. 11C: Shows FT-Raman differences between the different polymorphs (FIGS. 8, 9 and 10) for 760-810 cm$^{-1}$.

Crystalline polymorph Form IV of D-tartrate of compound I was obtained by equilibration in hot Ethanol (60° C.) and according to DSC has an endotherm at about 162° C. (see FIG. 6).

As used herein, by expressions like "crystalline form of a specific salt of compound I characterized by the X-Ray powder diffractogram shown in FIG. (1)" is meant the crystalline form of salt of compound I in question having an X-ray powder diffractogram substantially similar to FIG. (1), i.e. exhibiting an X-ray powder diffraction pattern substantially as exemplified in that Figure and measured under comparable conditions as described herein or by any comparable method. Generally, all data herein are understood to be approximate and subject to normal measurement error depending e.g. on the apparatus used and other parameters influencing peak positions and peak intensities.

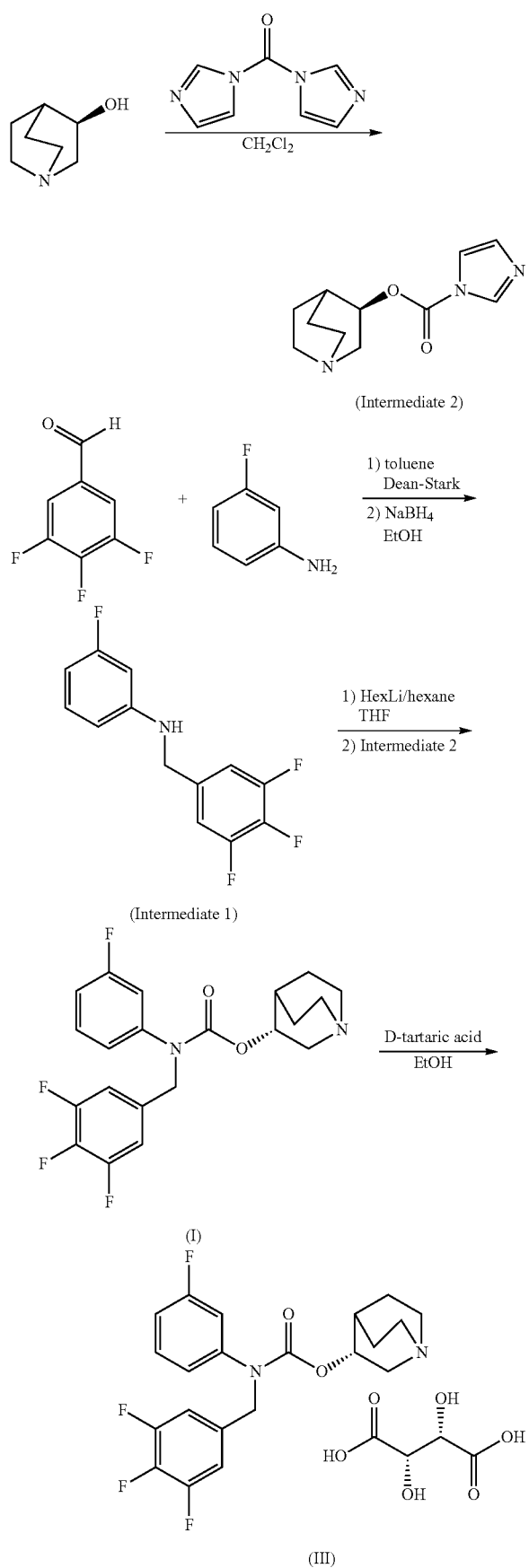

The reaction of (R)-3-Quinuclidinol with carbonyldiimidazole (CDI) in dichloromethane, at 0° C. during 4 h, afford the corresponding imidazolide carbamate (intermediate 2).

Intermediate 1 was obtained by imine formation between 3,4,5-trifluorobenzaldehyde and 3-fluoroaniline (in a Dean-Stark system) and later reduction with sodium borohydride in ethanol.

The key coupling reaction was carried out by deprotonation of the amine (intermediate 1) with hexyl lithium at −10° C. and subsequent addition of imidazolide (intermediate 2), in THF, at −10° C., stirring it during 2 h.

Finally, D-tartrate of compound I was obtained by crystallization in hot ethanol adding 1 equivalent of D-tartaric acid to the compound I.

An object of the invention is a pharmaceutical composition comprising the active pharmaceutical ingredient (D-tartrate of compound I) or mixture of the active pharmaceutical ingredient with other active pharmaceutical ingredients and/or pharmaceutically acceptable carriers or excipients.

Such pharmaceutical composition can be administered orally, in the form of powders, granulates, tablets, capsules, lozenges, multiparticulates, lyophilised forms, solutions or suspensions, transdermal or buccal patches, emulsions or microemulsions, for immediate-, or modified-release applications (sustained-, delayed- or pulsed-release applications). Such pharmaceutical composition, as described above, may be administered by direct intake or as soluble, dispersible, orodispersible, chewable, effervescent or bioadhesive dosage forms, or through the skin.

Powders and granulates may be obtained by direct mix o successive mix of their components or by dry or wet granulation, aqueous or organic. Powders and granulates may contain excipients such as diluents, binders, disintegrants, wetting agents, glidants, lubricants, plastificants, absorbent or adsorbent agents, immediate- or modified-release polymers, sweetening or flavouring agents, colouring matter or dyes agents, or preservatives and may be dosified as monodose or multidose pharmaceutical forms.

Tablets cited above may be obtained from powders, granulates, other tablets or lozenges or any combination thereof. These tablets may be any conventional, multilayer, effervescent, dispersible, soluble, orodispersible, gastro-resistant, modified release, bioadhesive, chewable, buccal or matricial dosage forms. These tablets may also be coated with one or more functional layers in order to protect the active pharmaceutical ingredient or modify its release. Any layer may contain the active pharmaceutical ingredient, alone or with one or more modified-release polymers. Tablets described above may contain excipients such as diluents, binders, disintegrants, wetting agents, glidants, lubricants, plastificants, absorbent or adsorbent agents, immediate- or modified-release polymers, sweetening or flavouring agents, colouring matter or dyes agents, or preservatives.

Capsules cited above may be manufactured from gelatin, HPMC, cellulosic or polysaccharide derivates, flour cereals or a combination thereof, and may be soft or hard capsules. Capsules may contain powders, granulates, multiparticulate pharmaceutical forms, tablets, lozenges, liquids or semisolids, or a combination thereof. These capsules may also be coated with one or more functional layers in order to protect the active pharmaceutical ingredient or modify its release. Any layer may contain the active pharmaceutical ingredient, alone or with one or more modified-release polymers. Capsules described above may contain excipients such as diluents, binders, disintegrants, wetting agents, glidants, lubricants, plastificants, absorbent or adsorbent agents, immediate- or modified-release polymers, sweetening or flavouring agents, colouring matter or dyes agents, or preservatives.

Multiparticulate pharmaceutical forms may be administered under a monodose or multidose way. These pharmaceutical forms may be administered as capsules, tablets, sachets or strips, suspensions, solutions, vials, flasks or bottles or any other device. Such multiparticulate pharmaceutical forms may be used for immediate or modified-release applications and obtained from an inert or active core containing the active pharmaceutical ingredient. Cores may be coated by one or more functional layers in order to protect or modify the release of the active pharmaceutical ingredient. This ingredient may be included in one or more layers, alone or with one or more modified-release polymers. Additional layers, including protecting agents or modified-release polymers may be included in other external layer next to the layer containing the active pharmaceutical ingredient. Such multiparticulate pharmaceutical forms may contain excipients such diluents, binders, disintegrants, wetting agents, glidants, lubricants, plasticants, absorbent or adsorbent agents, immediate- or modified-release polymers, sweetening or flavouring agents, colouring matter or dyes agents, or preservatives.

The liquid and semi-solid pharmaceutical forms, as solutions, suspensions, gels, emulsions, micro-emulsions and others, incorporate the active ingredient, in a soluble form, disperse or in a multiparticular form, and adequate excipients. They can be dosed in monodose or multidose form, being able to be of extemporaneous preparation. It can contain excipients such as emulsifiers, solubility enhancers, dispersants, humectants, co-emulsifiers, emollients, viscosity increasing agents, vehicles, preservatives, pH adjustment agents, flavouring agents or sweeteners. These components can be liquids of aqueous, lipidic or organic nature.

The active pharmaceutical ingredient may be released via the skin, or any suitable external surface, including mucosal membranes, such as those found inside the mouth. Transdermal or buccal patches may incorporate the drug into the device and be included in a matrix, in an adhesive or in a reservoir. Formulates may incorporate wetting agents, immediate- or modified-release polymers, enhancers, emulsifiers, dispersants, co-emulsifiers, solubility enhancers, adhesives, humectants, emollients, viscosity increasing agents, vehicles, preservatives or pH adjustment agents. These components can be semisolids or liquids, of aqueous, lipidic or organic nature. Matrix may be solid or semisolid in one or more layers. Patches include a permeable membrane on one side and also some form of adhesive to maintain the patch in place on the patient's skin, with the membrane in contact with the skin so that the medication can diffuse out of the patch reservoir and into and through the skin. The outer side of the patch is formed of an impermeable layer of material, and the membrane side and the outer side are joined around the perimeter of the patch, forming a reservoir for the medication and carrier between the two layers.

EXAMPLES

Analytical Methods $^1$H-NMR and $^{13}$C-NMR spectra was recorded at 400 MHz and 100.61 MHz respectively on a Bruker ARX 400 instrument. Dimethyl sulfoxide (99.8% D) was used as solvent, and tetramethylsilane (TMS) was used as internal reference standard.

The purity of D-tartrate of compound I was determined by HPLC/MS using a Gemini 5 u C18 110A, 50×4.6 mm column at 25° C. The mobile phase was 70% of solution A (0.025 M orthophosphoric acid at pH 3.0-3.1 with triethylamine) and 30% of solution B (Acetonitrile/methanol (9:1)) at a flow rate of 1.4 ml/minute. Run time 20 min. Detection was performed using a UV detector at 200 nm. D-tartrate of compound I showed a retention time of approximately 6.5 min.

The enantiomeric excess of compound I was determined by using a Quirabiotic V-2 column, 25×0.46 cm L, at 25° C. The mobile phase 0.1% (w/v) trifluoroacetic acid in methanol adjusted to pH about 6.5 with ammonium hydroxide at a flow rate of 0.5 ml/min, run time 25 min. Detection was performed using a UV detector at 230 nm. D-tartrate of compound I had a retention time of approximately 16 min, and its enantiomer had a retention time of approximately 17 min.

The Melting points were measured using Differential Scanning calorimetry (DSC). The equipment was a Perkin Elmer DSC 7 or a Perkin Elmer Pyris 1 with various crucibles (gold, alumina, open, closed, microhole), heating rate variable and range variable.

X-Ray powder diffractograms were measured on a Philips X'Pert PW 3040 or Philips PW 1710 using Cu kα radiation. The samples were measured in reflection mode in the 2θ-range 2-50°

FT-Raman Spectroscopy was registered on a Bruker RFS100 equipment. Nd:YAG 1064 nm excitation, 100 mW laser power, Ge-detector, 64 scans, range 25-3500 cm$^{-1}$, 2 cm$^{-1}$ resolution.

TG-FTIR: Netzsch Thermo-Microbalance TG 209 with Bruker FT-IR Spectrometer Vector 22. Al-crucible (open or with Microhole); $N_2$ atmosphere, heating rate 10° C. min$^{-1}$, range 25-250° C.

Dynamic Vapour Sorption (DVS). The equipment was a Surface Measurement Systems Ltd. DVS-1 Water vapour sorption analyser. The sample was placed on a quartz or platinum holder on top of a microbalance, and the sample was allowed to equilibrate at 50% r.h. before starting a pre-defined humidity program.

Specific rotation measurements were performed using a polarimeter from Schmidt+Haensch, model Polartronic-E (series number 27586), equipped with a thermostatic bath from Techne, model TE-8J.

Synthesis

Example 1

Synthesis of (R)-3-fluorophenyl-3,4,5-trifluorobenzylcarbamic acid 1-azabicyclo[2.2.2]oct-3-yl ester (compound I)

Intermediate 2

(R)-imidazole-1-Carboxylic acid 1-azabicyclo[2.2.2]oct-3-yl ester

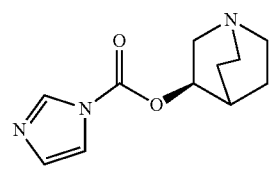 [SMILES: O=C(O[C@H]1CN2CCC1CC2)n1ccnc1]

To a suspension of 1.86 Kg of (R)-3-quinuclidinol in 30 L of dichloromethane, 2.92 Kg of DCI were added at 0° C. The solution was stirred during 3 h under inert atmosphere. Then, 23 L of water were added and extracted. The organic layer was dried over anhydrous sodium sulfate. The solvent was distilled off under reduced pressure. The obtained white solid was crystallized with isopropyl acetate (IPAC)-heptane to give 24.1 Kg of the title compound.

IR (KBr, cm$^{-1}$): 1746;
$^{1}$H-NMR: 1.33-1.43 (m, 1H); 1.47-1.57 (m, 1H); 1.58-1.70 (m, 1H); 1.75-1.87 (m, 1H); 2.07-2.12 (m, 1H); 2.56-2.90 (m, 5H); 3.18 (ddd, J=14.5, J=8, J=2, 1H); 4.95-5.00 (m, 1H); 7.07 (s, 1H); 7.61 (s, 1H); 8.29 (s, 1H).
$^{13}$C-NMR: 18.9; 23.7; 24.9; 45.7; 46.6; 54.1; 75.7; 117.3; 130.1; 137.1; 147.9.

Intermediate 1

(3-Fluorophenyl)-(3,4,5-trifluorobenzyl)amine

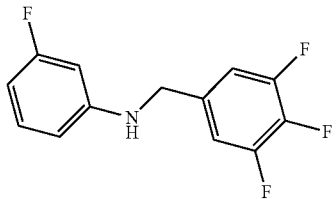 [SMILES: Fc1cccc(NCc2cc(F)c(F)c(F)c2)c1]

In a 300 L reactor fitted with a Dean-Stark funnel and refluxing condenser, toluene (63 L), 3,4,5-trifluorobenzaldehyde (2.1 Kg) and 3-fluoroaniline (1.33 Kg) were refluxed (112° C.) during 10 h.

After cooling, the resulting solution was concentrated to give the imine as an oil in a quantitative yield (3.2 Kg). Then ethanol (35 L) and sodium borohydride (0.5 Kg) was added. The resulting suspension was stirred 3 h, Then, 42 L of water were added, the ethanol was distilled off and the aqueous layer extracted with dichloromethane (2×40 L). The organic layer was dried over anhydrous sodium sulfate. The solvent was distilled off under reduced pressure giving 2.72 kg of the title compound as an yellow oil.

1H-NMR: 4.29 (s, 2H); 4.33 (br., 1H); 6.28 (dtd, J=11, J=2.5; J=1, 1H), 6.40 (ddd, J=8.5; J=2, J=1, 1H), 6.46 (tdt, J=8.5; J=2.5; J=1); 7.24 (dd, J=8; J=7, 2H); 7.14 (tdd, J=8; J=6.5, J=1).
$^{13}$C-NMR: 47.1; 99.9 (d, J=25.5); 104.8 (d, J=21); 109.1 (d, J=2); 111.0 (d, J=10.5); 111.0 (d, J=21.5); 149.4 (dd, J=11, J=1); 136.0 (tdd, J=6, J=4, J=2); 139.0 (dt, J=248, J=5); 151.6 (ddd, J=248, J=10, J=4); 164.3 (d, J=241).

Compound I (R)-3-Fluorophenyl-3,4,5-trifluorobenzylcarbamic acid 1-azabicyclo[2.2.2]oct-3-yl ester To a solution of 2.72 Kg of intermediate (1) in 17 L of THF, cooled at −10° C., were added slowly (2 h), under inert atmosphere, 3 Kg of hexyl Lithium (33% in hexanes) and the resulting mixture was stirred for 1 h at −10° C. Then at −10° C. 2.41 Kg of intermediate 2 in 23 L of THF were slowly added (75 min). The resulting mixture was stirred for 2 h and allowed to rise room temperature, then water was added and the solution was extracted with methyl tertbuthylether. The organic phase was dried over anhydrous sodium sulfate and the solvent was removed under reduced pressure giving 3.6 kg of the title compound as an orange oil.

Example 2

Synthesis of (R)-3-Fluorophenyl-3,4,5-trifluorobenzylcarbamic acid 1-azabicyclo[2.2.2]oct-3-yl ester (compound I) D-tartrate salt To a solution of 3 Kg of (R)-3-fluorophenyl-3,4,5-trifluorobenzylcarbamic acid 1-azabicyclo[2.2.2]oct-3-yl ester (compound I) in ethanol (3 L) at 60° C., 1.1 Kg D-tartaric acid in 30 L of ethanol, warmed at 60° C. were added and the resulting mixture stirred 1 h and then cooled to below room temperature and kept at this temperature for 1 hour. The precipitate is filtered off and the filter cake is washed with ethanol (8 L). The filter cake is sucked free of most of the solvent, and the product is dried at 45° during 16 h. Yielding 3.5 kg of the title compound as a white crystalline solid.

$^{1}$H-NMR: 1.45-1.49 (m, 2H) 1.65-1.75 (m, 2H), 2.05 (m, 1H); 2.87-3.01 (m, 3H); 3.07-3.11 (m, 1H); 3.08-3.11 (d, J=14, 1H); 3.39-3.45 (ddd, J=12, J=8, J=2, 1H); 4.00 (s, 2H); 4.83-4.89 (m, 1H); 4.84-4.89 (d, J=16.5, 1H); 4.93-4.97 (d, J=16.5, 1H); 7.05 (td, J=8.5; J=2, 1H); 7.21 (dd, J=8; J=1.5, 1H); 7.24 (dd, J=8.5; J=7, 2H), 7.33-7.38 (m, 2H).
$^{13}$C-NMR: 17.1; 20.4; 24.0; 44.5; 45.1; 51.6; 52.7; 69.5; 72.1; 111.8 (d, J=19.5); 113.4 (d, J=20.5); 114.1 (d, J=22); 122.6; 130.3 (d, J=9); 135.1; 137.8 (dt, J=246, J=16); 142.6 (d, J=9); 150.2 (ddd, J=246, J=9.5, J=3.5); 154.0; 161.9 (d, J=242); 174.7

Elemental Analysis. Calculated for $C_{25}H_{26}F_4N_2O_8$: C, 53.77; H, 4.69; N, 5.02. Found: C, 53.63; H, 4.73; N, 5.01

An XRPD pattern for the crystals prepared is shown in FIG. 1.

Specific rotation was determined. 1.00 g of substance was diluted with methanol in a 100 mL volumetric flask. α (c=1, MeOH) c=g/100 mL. The measured specific rotation was −35.2°.

On the other hand, the equilibrium solubility of the D-tartrate salt with several solvents was measured at 25° C. and was found to be (measured as the free base) as indicated in Table 2.

TABLE 2

| Solvent | Solubility (mg/ml) |
| --- | --- |
| Methanol | 258.5 |
| Ethanol | 10 |
| Isopropyl alcohol | 1.5 |
| Dichloromethane | 2.2 |
| Hexane | 0.3 |
| n-Octanol | 0.5 |
| Water | 250.8 |
| 0.1 Hydrochloric acid | 366.6 |
| 0.1N sodium hydroxide | 0.09 |

Evaluation of Hygroscopicity: No significant mass gain or mass loss was observed at 93% RH or below conditions. A significant water addition issue was observed at 97% RH, but no hygroscopicity issues related to standard atmospheric conditions are expected as shown in Table 3.

TABLE 3

| | HYGROSCOPICITY STUDY (KF initial = 0.9692%) | | | | | | | | | |
|---|---|---|---|---|---|---|---|---|---|---|
| Time (h) | 12% RH | 22% RH | 33% RH | 43% RH | 53% RH | 64% RH | 75% RH | 85% RH | 93% RH | 97% RH |
| 4 | −0.26 | −0.16 | −0.25 | −0.38 | −0.19 | −0.08 | −0.08 | 0.16 | 0.16 | 1.51 |
| 8 | −0.20 | −0.26 | −0.24 | −0.32 | −0.21 | −0.07 | 0.02 | 0.13 | 0.03 | 1.06 |
| 14 | −0.30 | −0.25 | −0.21 | −0.21 | −0.16 | −0.07 | 0.01 | 0.22 | 0.24 | 4.36 |
| 48 | −0.04 | −0.21 | −0.19 | −0.25 | −0.17 | 0.02 | 0.06 | 0.26 | 0.44 | 7.86 |
| 72 | −0.28 | −0.24 | −0.23 | −0.31 | −0.16 | −0.07 | 0.01 | 0.14 | 0.41 | 10.88 |
| 96 | −0.30 | −0.26 | −0.17 | −0.30 | −0.19 | −0.07 | −0.06 | 0.07 | 0.40 | 13.77 |
| 144 | −0.33 | −0.18 | −0.30 | −0.40 | −0.17 | 0.15 | −0.08 | 0.24 | 0.43 | 23.58 |
| 168 | −0.32 | −0.28 | −0.39 | −0.34 | −0.16 | 0.15 | −0.05 | 0.18 | 0.39 | 23.62 |
| 192 | −0.27 | −0.21 | −0.11 | −0.19 | −0.20 | 0.20 | 0.00 | 0.15 | 0.38 | 23.06 |
| 216 | −0.29 | −0.19 | −0.15 | −0.25 | −0.14 | 0.25 | 0.01 | 0.23 | 0.43 | 22.13 |
| 240 | −0.08 | −0.11 | −0.18 | −0.18 | 0.00 | 0.59 | 0.29 | 0.59 | 0.81 | 19.88 |

Example 3

Preparation of Form II of D-Tartrate of Compound I

Form I (Example I) was treated as follows in DSC: Closed pan (STGF), 0.0295 g, 25 to 143.5° C., 2° C. min$^{-1}$, scan down to 130° C., hold isotherm for 15 minutes, cool to 25° C.

Example 4

Preparation of Form III of Compound I D-Tartrate 0.49 g of form I were suspended in 1 mL of water and then shaken at 20° C. during 10 minutes (until dissolution), after 2 h the sample was thickened.

Example 5

Preparation of Form IV of Compound I D-Tartrate 0.522 g of form I were suspended in 1 mL of EtOH abs. and then shaken at 60° C., After 1 day the suspension disappeared and a new white crystalline crust was formed above the solvent sticking on the container wall.

The invention claimed is:

1. A D-tartrate salt of compound I ((R)-3-fluorophenyl-3,4,5-trifluorobenzylcarbamic acid 1-azabicyclo[2.2.2]oct-3-yl ester) of structural formula:

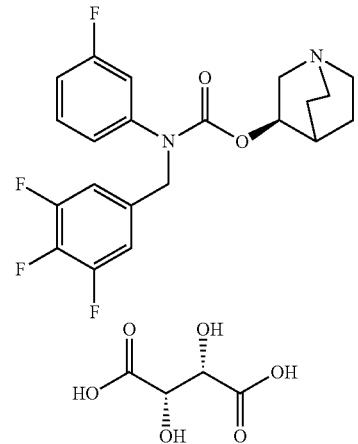

possessing a stoichiometry of substantially 1:1 of compound I to D-tartaric acid, and in the form of crystalline polymorph I, which is characterized by an X-Ray powder diffractogram pattern with peaks at ° 2θ as shown in FIG. 1.

2. The salt of claim 1, which is a substantially anhydrous crystalline salt.

3. A pharmaceutical composition comprising a salt of claim 1 with at least one pharmaceutically acceptable carrier or excipient.

4. A salt according to claim 1 for use as a medicament.

5. A pharmaceutical composition comprising a salt of claim 2 with at least one pharmaceutically acceptable carrier or excipient.

6. A salt according to claim 2 for use as a medicament.

\* \* \* \* \*

UNITED STATES PATENT AND TRADEMARK OFFICE
CERTIFICATE OF CORRECTION

| | | |
|---|---|---|
| PATENT NO. | : 8,492,402 B2 | Page 1 of 1 |
| APPLICATION NO. | : 12/744493 | |
| DATED | : July 23, 2013 | |
| INVENTOR(S) | : Juan Lorenzo Catena Ruiz et al. | |

It is certified that error appears in the above-identified patent and that said Letters Patent is hereby corrected as shown below:

Title Page, item [75] Inventor José Hidalgo Rodriguez, City, Change "Esplugues de Lilobregat-" to --Esplugues de Llobregat--

Signed and Sealed this
Twenty-ninth Day of October, 2013

Teresa Stanek Rea
*Deputy Director of the United States Patent and Trademark Office*